United States Patent [19]

Tonks et al.

[11] Patent Number: 5,073,667

[45] Date of Patent: Dec. 17, 1991

[54] PROCESS FOR THE ISOMERIZATION OF A HYDROCARBON FEED

[75] Inventors: Gregory V. Tonks; Anne E. L. M. M. Verstappen Declercq, both of The Hague, Netherlands

[73] Assignee: Shell Oil Company, Houston, Tex.

[21] Appl. No.: 594,467

[22] Filed: Oct. 9, 1990

[30] Foreign Application Priority Data

Apr. 11, 1990 [GB] United Kingdom ............... 9008289

[51] Int. Cl.$^5$ ............................................... C07C 5/13
[52] U.S. Cl. ..................................... 585/738; 585/734; 585/750; 585/826; 585/751
[58] Field of Search ............... 585/738, 737, 826, 750, 585/751; 208/134

[56] References Cited

U.S. PATENT DOCUMENTS

| | | |
|---|---|---|
| 3,755,144 | 8/1973 | Asselin .............................. 208/95 |
| 4,275,257 | 6/1981 | Hutson .............................. 585/738 |
| 4,717,784 | 1/1988 | Stein et al. ........................ 585/738 |
| 4,804,802 | 2/1989 | Evans et al. ...................... 585/738 |

Primary Examiner—Anthony McFarlane
Assistant Examiner—Nhat Phan

[57] ABSTRACT

Process for the isomerization of a hydrocarbon feed containing hydrocarbons comprising at least 4 carbon atoms, which process comprises isomerizing a hydrocarbon stream; separating the isomerisate thus obtained into a hydrogen-containing gas and a hydrocarbon effluent; separating from the hydrocarbon effluent a product stream containing branched hydrocarbons, leaving non-product hydrocarbons, and passing at least part of these hydrocarbons again to the isomerization step, in which process at least part of the feed is added to at least part of the isomerisate before the isomerisate is separated into the hydrogen-containing gas and the hydrocarbon effluent.

11 Claims, 1 Drawing Sheet

5,073,667

PROCESS FOR THE ISOMERIZATION OF A HYDROCARBON FEED

FIELD OF THE INVENTION

The present invention is concerned with the isomerization of a hydrocarbon feed containing hydrocarbons comprising at least 4 carbon atoms.

BACKGROUND OF THE INVENTION

From U.S. Pat. No. 3,755,144 a process is known in which a low octane hydrocarbon charge stock is isomerized to produce a branched hydrocarbon product. The process comprises isomerizing the charge stock in an isomerization zone and separating the effluent into a hydrogen-rich gaseous phase and hydrocarbon effluent. Hydrocarbon effluent containing 5 or 6 carbon atoms is passed to a molecular sieve separation zone, to provide a normal hydrocarbons stream and a branched hydrocarbons stream. The normal hydrocarbons stream is mixed with fresh charge stock and is again sent to the isomerization zone.

It has now surprisingly been found that by introducing feed into the process by adding fresh feed to the effluent of the isomerization step before separating off a hydrogen-containing gas, a better separation of hydrogen-containing gas and hydrocarbon effluent is obtained, with the same conventional separation means being used. A better separation makes that the volume of the hydrogen-containing gas is decreased, as the amount of hydrocarbons still present is decreased and therefore smaller units can be employed for further processing of the hydrogen-containing gas, resulting in lower operating costs.

SUMMARY OF THE INVENTION

Therefore, the present invention relates to a process for the isomerization of a hydrocarbon feed containing hydrocarbons comprising at least 4 carbon atoms, which process comprises the following process steps:
a) isomerizing a hydrocarbon stream in the presence of hydrogen, and an isomerization catalyst, yielding an isomerisate;
b) separating at least part of the isomerisate of step a) into a hydrogen-containing gas and a hydrocarbon effluent;
c) contacting at least part of the hydrocarbon effluent with a separatory molecular sieve capable of adsorbing normal hydrocarbons, whereby a product stream containing branched hydrocarbons is separated and other hydrocarbons are adsorbed;
d) desorbing adsorbed hydrocarbons from the separatory molecular sieve; and
e) passing at least part of the hydrocarbons thus desorbed to isomerization step a),
in which process at least part of the feed is added to at least part of the isomerisate of step a) before the isomerisate is separated in step b).

DETAILED DESCRIPTION OF THE INVENTION

The hydrocarbons which are adsorbed on the separatory molecular sieve in step c), can be desorbed therefrom by contacting the sieve with a liquid solvent or with a gas. Preferably, in step d) adsorbed hydrocarbons are desorbed by passing a hydrogen-containing gas over the molecular sieve.

When a hydrogen-containing gas is used for desorbing adsorbed hydrocarbons, the process can further comprise adding feed to at least part of the effluent of step d), containing desorbed hydrocarbons and hydrogen; separating at least part of the mixture of effluent and feed into a hydrogen-containing gas and a stream containing desorbed hydrocarbons; and passing at least part of the stream containing desorbed hydrocarbons to isomerization step a).

The feed which is introduced into the process comprises hydrocarbons comprising at least 4 carbon atoms, suitably hydrocarbons with 4 to 7 carbon atoms. The feed can contain minor amounts of lighter hydrocarbons. Generally, the feed will mainly contain hydrocarbons comprising at least 5 carbon atoms, preferably hydrocarbons with 5 and 6 carbon atoms. Preferably 10 to 100%w of the feed is added to at least part of, advantageously to the complete, isomerisate of step a) before separation in step b).

The isomerization in step a) is suitably carried out at a temperature between 100° and 350° C. and a pressure between 1 and 50 bar. The isomerization catalyst employed suitably is a heterogeneous hydroisomerization catalyst having an acid activity and a hydrogenation activity and comprising one or more metals from Group VIII of the Periodic Table of the Elements on a carrier material. The carrier material has acidic properties and may suitably consist of silica-alumina, in particular zeolites (e.g. mordenite, faujasite or Y-sieve) in the hydrogen form or exchanged with rare earth ions, or of alumina rendered acidic by combination with halogen (e.g. chlorine). Preferably, the employed catalyst comprises a noble metal from Group 8 of the Periodic Table of the Elements (in particular platinum) on a carrier containing mordenite, preferably H-mordenite. Most preferably, the H-mordenite is prepared by treating mordenite one or more times with an aqueous solution of an ammonium compound (e.g. ammonium nitrate), followed by drying (e.g. at 100°-200° C.) and calcining (e.g. at 400°-700° C.) the treated mordenite.

At least part of the isomerisate is passed to separation step b) in which a hydrogen-containing gas and a hydrocarbon effluent are separated. Suitably, in separation step b) a hydrogen-containing gas and a hydrocarbon effluent are separated by flash distillation. Suitably the flash distillation is carried out at a temperature between −20° and 100° C., and a pressure between 1 and 50 bar.

In separation step c), a separatory molecular sieve is used capable of adsorbing normal hydrocarbons. Suitably, unbranched hydrocarbons are substantially adsorbed, whereas branched and cyclic hydrocarbons are not retained in any substantial amount by the molecular sieve. This selectivity is dependent to a large extent on the pore diameters of the molecular sieve, which diameters are preferably in the range from 0.3-0.8 nm, most preferably from 0.4-0.6 nm. Suitably the hydrocarbon separation step comprises a separatory molecular sieve having a pore size which is sufficient to permit entry of normal hydrocarbons containing 4-7 carbon atoms, but restrictive enough to prohibit entry of $C_4$-$C_7$ mono-methyl branched, dimethyl branched and cyclic hydrocarbons. Suitably, synthetic or natural zeolites, erionite and offretite are used as molecular sieve, and preferably zeolite 5A. The particles which comprise molecular sieve material may in addition comprise a binder material such as alumina, silica or silica-alumina, in order to improve the crushing strength of the particles; said particles may also be mixed with particles which do not contain molecular sieve material.

Hydrocarbons which are adsorbed on the separatory molecular sieve, can be periodically desorbed therefrom by interrupting the stream of hydrocarbon effluent and passing a hydrogen-containing gas over the separatory molecular sieve. After desorption of a substantial amount of the adsorbed hydrocarbons, the stream of hydrogen-containing gas is interrupted and the stream of hydrocarbon effluent from the isomerization step is contacted again with the sieve. It is possible to carry out the process such that a continuous stream containing normal hydrocarbons is obtained, e.g. by using several vessels. The hydrogen-containing gas which can be used for desorbing the adsorbed hydrocarbons, need not be completely pure and may contain a certain amount of other components, suitably not more than 40 mol % and preferably not more than 20 mol % of other compounds such as hydrocarbons, e.g. reformer off-gas, provided that these compounds are substantially inert with respect to the feed and the separatory molecular sieve applied. The hydrogen-containing gas is suitably passed over the molecular sieve at a temperature of between 100° and 450° C. and a pressure of between 1 and 50 bar.

If feed is added to at least part of the effluent of step d) containing desorbed hydrocarbons and hydrogen, separation of at least part of the mixture of effluent and feed into a hydrogen-containing gas and hydrocarbon effluent, is suitably carried out by flash distillation. The flash distillation can suitably be carried out at a temperature between $-20°$ and $100°$ C., and a pressure between 1 and 50 bar.

The process according to the present invention can be carried out in a number of alternative ways, and some process schemes according to the present invention will be elucidated more fully hereinafter, with reference to the accompanying figures.

DETAILED DESCRIPTION OF THE FIGURES

The processes of the figures are carried out with the help of an isomerization unit (10), a first separation unit (20), a hydrocarbon separation unit (30) and optionally a second separation unit (40).

Figure 1:
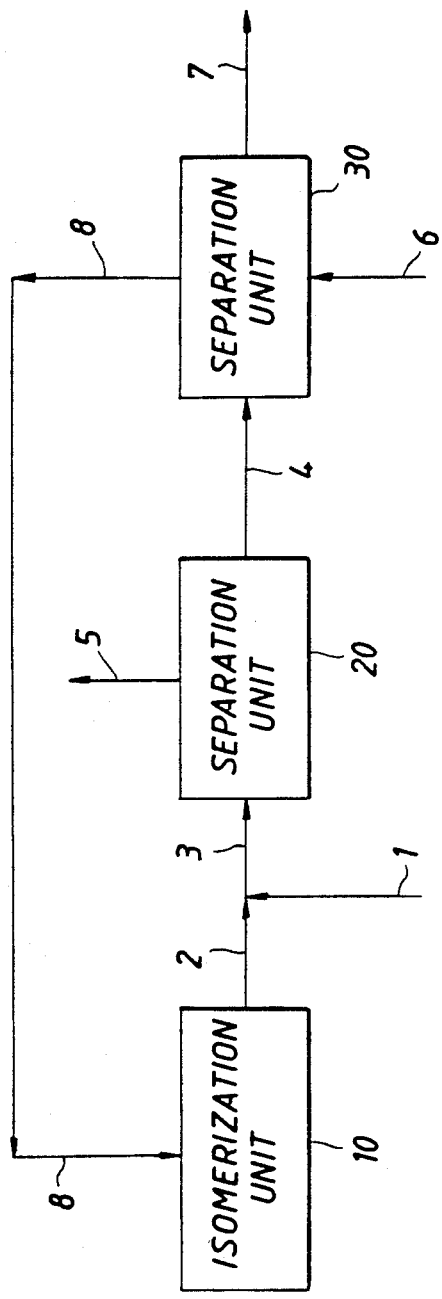
FIG. 1 represents a flow scheme of an embodiment of the present process.

In the process schematically shown in FIG. 1, a hydrocarbon stream (8), described hereinafter, is passed to isomerization unit (10) in which the stream is contacted in the presence of hydrogen with an isomerization catalyst at isomerization conditions. Fresh feed (1) is added to at least part of isomerisate (2), and together they are sent to the first separation unit (20). In first separation unit (20) a hydrogen-containing gas is separated from hydrocarbon effluent with the help of flash distillation. The hydrogen-containing gas (5) is removed and hydrocarbon effluent (4) is passed to hydrocarbon separation unit (30). The separation unit (30) comprises a separatory molecular sieve having a pore size which is sufficient to permit entry of normal hydrocarbons containing 4-7 carbon atoms, but restrictive enough to prohibit entry of $C_4$-$C_7$ mono-methyl branched and dimethyl branched hydrocarbons. Hydrocarbon effluent (4) is passed over the molecular sieve, giving a product stream containing mainly branched hydrocarbons (7). Periodically at least part of the adsorbed normal hydrocarbons is desorbed from the separatory molecular sieve by interrupting the stream of hydrocarbon effluent and passing a hydrogen-containing gas (6) over the separatory molecular sieve. After desorption of a substantial amount of the adsorbed hydrocarbons, the stream of hydrogen-containing gas (6) is interrupted and the stream of hydrocarbon effluent from the isomerization unit is again contacted with the sieve. At least part of the effluent containing desorbed hydrocarbons and hydrogen, (8), is passed to isomerization unit (10).

Figure 2:
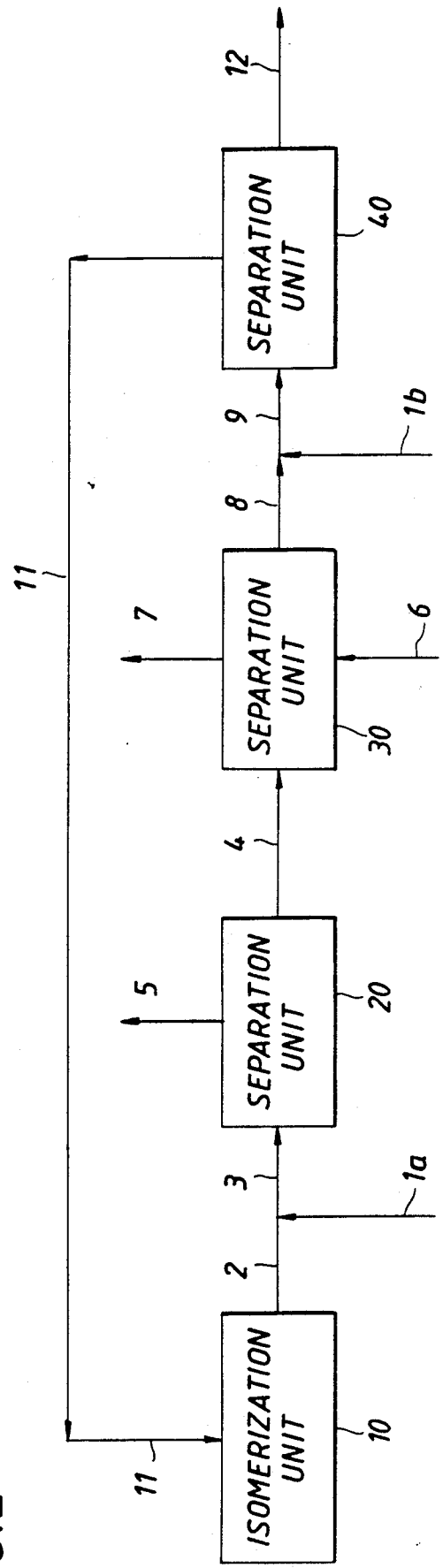
FIG. 2 represents a flow scheme of another embodiment in which part of the feed is added to the effluent of step d).

In FIG. 2 a process is schematically shown, in which a hydrocarbon stream (11), described hereinafter, is passed to isomerization unit (10) in which the stream is contacted in the presence of hydrogen with an isomerization catalyst at isomerization conditions. Fresh feed (1a) is added to at least part of isomerisate (2), and together they are sent to the first separation unit (20), in which a hydrogen-containing gas (5) and a hydrocarbon effluent (4) are separated. Hydrogen-containing gas (5) is removed, and the hydrocarbon effluent (4) is passed to hydrocarbon separation unit (30), which separation unit comprises a separatory molecular sieve. The hydrocarbon effluent (4) is passed over the molecular sieve, thereby producing a product stream containing mainly branched hydrocarbons (7). Adsorbed hydrocarbons are desorbed with the help of hydrogen-containing gas (6). A mixture (9) comprising the effluent containing hydrogen and desorbed hydrocarbons (8) and fresh feed (1b) is passed to second separation unit (40). In the second separation unit (40), the mixture (9) of effluent and feed is separated into a hydrogen-containing gas (12) and a stream containing desorbed hydrocarbons (11), which latter stream is passed to isomerization unit (10).

What is claimed is:

1. Process for the isomerization of a hydrocarbon feed containing hydrocarbons comprising at least 4 carbon atoms, which process comprises the following process steps:
    a) isomerizing a hydrocarbon stream in the presence of hydrogen, and an isomerization catalyst yielding an isomerisate;
    b) separating at least part of the isomerisate of step a) into a hydrogen-containing gas and a hydrocarbon effluent;
    c) contacting at least part of the hydrocarbon effluent with a separatory molecular sieve capable of adsorbing normal hydrocarbons, whereby a product stream containing branched hydrocarbons is separated and other hydrocarbons are adsorbed;
    d) desorbing adsorbed hydrocarbons from the separatory molecular sieve; and
    e) passing at least part of the hydrocarbons thus desorbed to isomerization step a), in which process at least part of the feed is added to at least part of the isomerisate of step a) before the isomerisate is separated in step b).

2. Process according to claim 1, wherein in step d) adsorbed hydrocarbons are desorbed by passing a hydrogen-containing gas over the molecular sieve yielding an effluent of step d) containing desorbed hydrocarbons and hydrogen.

3. Process according to claim 2, which process comprises adding feed to at least part of the effluent of step d); separating a hydrogen-containing gas from at least part of the mixture of effluent of step d) and feed to yield a stream containing desorbed hydrocarbons; and passing at least part of the stream containing desorbed hydrocarbons to isomerization step a).

4. Process according to claim 1, wherein isomerization step a) is carried out at a temperature between 100° and 350° C. and a pressure between 1 and 50 bar.

5. Process according to claim 1, wherein the isomerization catalyst comprises platinum on a carrier containing mordenite.

6. Process according to claim 1, wherein in separation step b) the hydrogen-containing gas and the hydrocarbon effluent are separated by flash distillation.

7. Process according to claim 6, wherein the flash distillation is carried out at a temperature between −20° and 100° C. and at a pressure between 1 and 50 bar.

8. Process according to claim 1, wherein in step c) a separatory molecular sieve is used having a pore size which is sufficient to permit entry of normal hydrocarbons containing 4–7 carbon atoms, but restrictive enough to prohibit entry of $C_4$-$C_7$ mono-methyl branched, dimethyl branched and cyclic hydrocarbons.

9. Process according to claim 2, wherein the hydrogen-containing gas is passed over the molecular sieve at a temperature of between 100° and 450° C. and at a pressure between 1 and 50 bar.

10. Process according to claim 3, wherein at least part of the mixture of effluent of step d) and feed is separated into the hydrogen-containing gas and the stream containing desorbed hydrocarbon by flash distillation.

11. Process according to claim 10, wherein the flash distillation is carried out at a temperature between −20° and 100° C. and at a pressure between 1 and 50 bar.

* * * * *